United States Patent
Raynal-Olive et al.

(10) Patent No.: US 7,303,073 B2
(45) Date of Patent: Dec. 4, 2007

(54) PACKAGING FOR STERILE OBJECTS OR OBJECTS TO BE STERILIZED

(75) Inventors: Claire Raynal-Olive, Le Genevrey (FR); Jean-Pierre Grimard, Vif (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 192 days.

(21) Appl. No.: 10/511,579

(22) PCT Filed: Apr. 18, 2003

(86) PCT No.: PCT/FR03/01260

§ 371 (c)(1),
(2), (4) Date: May 9, 2005

(87) PCT Pub. No.: WO03/089028

PCT Pub. Date: Oct. 30, 2003

(65) Prior Publication Data

US 2005/0226763 A1  Oct. 13, 2005

(30) Foreign Application Priority Data

Apr. 22, 2002  (FR) ................... 02 04996

(51) Int. Cl.
*A61B 17/06* (2006.01)
*A61L 2/20* (2006.01)
*A65B 55/02* (2006.01)

(52) U.S. Cl. .................. 206/439; 206/370; 422/26; 422/300; 53/425

(58) Field of Classification Search ........ 206/438–439, 206/363–370, 570–572; 34/284–301; 422/26–28, 422/292–300; 53/396, 425
See application file for complete search history.

(56) References Cited

U.S. PATENT DOCUMENTS

| 4,055,672 | A | * | 10/1977 | Hirsch et al. | ................ 206/439 |
| 6,164,044 | A | * | 12/2000 | Porfano et al. | ................ 422/28 |
| 6,412,639 | B1 | * | 7/2002 | Hickey | ................ 206/438 |
| 6,566,144 | B1 | * | 5/2003 | Madril et al. | ................ 436/177 |
| 6,629,602 | B1 | * | 10/2003 | Heyman | ................ 206/438 |
| 6,722,054 | B2 | * | 4/2004 | Yarborough et al. | ........... 34/284 |
| 7,100,768 | B2 | * | 9/2006 | Grimard et al. | ............ 206/438 |
| 2005/0224382 | A1 | * | 10/2005 | Raynal-Olive et al. | ..... 206/438 |
| 2006/0054523 | A1 | * | 3/2006 | Porret et al. | ................ 206/439 |

* cited by examiner

*Primary Examiner*—Byron P. Gehman
(74) *Attorney, Agent, or Firm*—David M. Fortunato; Cohen Pontani Lieberman & Pavane LLP

(57) ABSTRACT

A package for transporting objects which are sterile or which are to be sterilized. The package has a box for accommodating objects, and a covering sheet made of a leak tight material which is fastened to the box so as to seal the box in a leak tight manner. The package has a layer of a material forming a screen which is at least partial with respect to a decontamination gas and/or able to absorb a decontamination gas. The layer is sized to be placed in the box along the covering sheet such that the layer lies above the objects. A plate or grill is provided with projections and is shaped, depending on the position of the package, to allow unrestricted diffusion of the sterilization gas over the objects, and to restrict or prevent diffusion of the decontamination gas over these same objects.

18 Claims, 1 Drawing Sheet

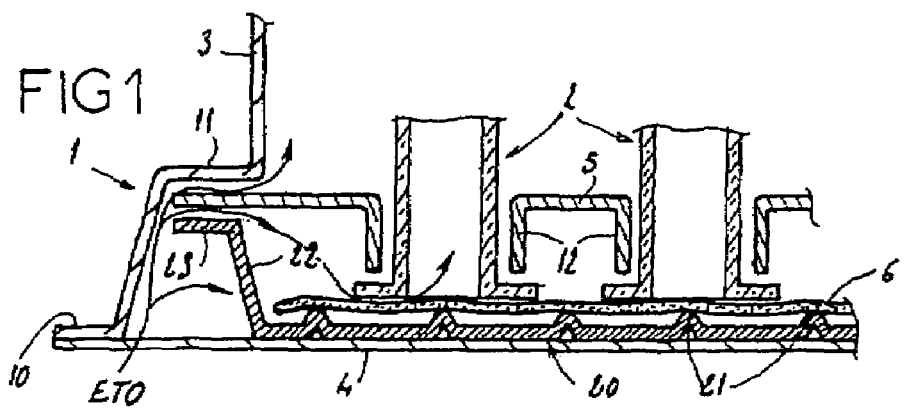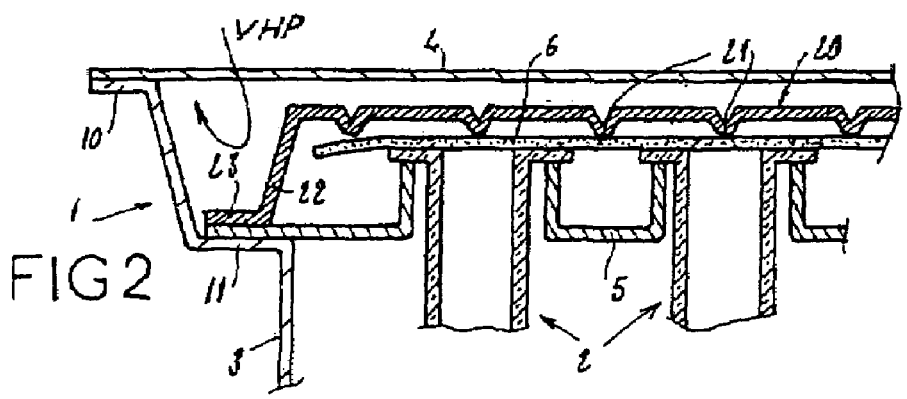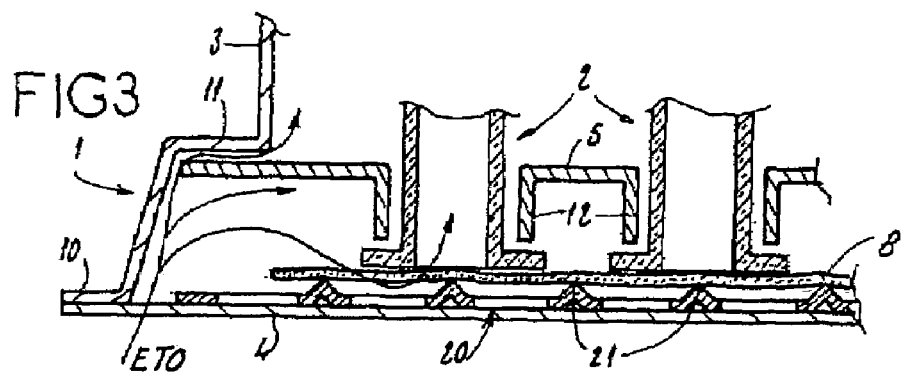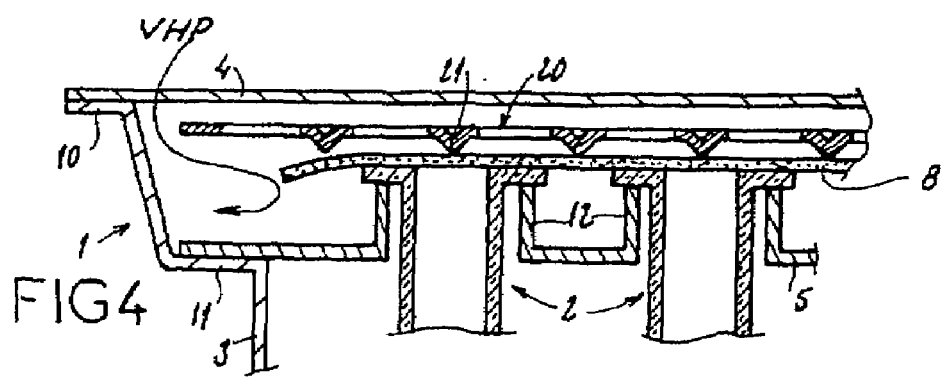

PACKAGING FOR STERILE OBJECTS OR OBJECTS TO BE STERILIZED

BACKGROUND OF THE INVENTION

The present invention relates to a package intended to be used to transport objects which are sterile or to be sterilized, to a process for manufacturing this package, to a sterilization and decontamination process using this package, and to the use of this package in a sterilization and decontamination process.

The package according to the invention may especially be used to transport syringe components, particularly syringe bodies intended to be filled subsequently by an active product or a medication.

The sterile conditions, under which some steps of handling or transporting objects intended for medical use have to take place, are very restrictive, in particular in the pharmaceutical industry. It is therefore very important to produce packages which are compatible with such requirements.

In the rest of the description, mention will be made of a selectively leaktight material which needs to be defined. The term "selectively leaktight", as used in the present description and in the claims, means that the material is designed, in terms of structure, so as to control any exchange on either side of said material, and thus especially from the inside of the package to the external environment thereof. This means, inter alia, that the package is leaktight, individually or in combination, to contamination by microorganisms, bacteria and/or biologically active material, which may come into contact with the package during its handling, while remaining permeable to a sterilization gas, for example of the ETO (ethylene oxide) type.

DESCRIPTION OF THE PRIOR ART

It is known to place objects which are sterile or to be sterilized into a plastic box, then to fasten a covering sheet made of a selectively leaktight material over this box so as to seal the latter, to place the package thus formed into a second package comprising a window closed by a sheet made of a selectively leaktight material, and to sterilize the unit as a whole with a gas of the ETO type. The package sterilized in this way is placed in a box, for example made of cardboard, for dispatch; at its destination, the cardboard box and said second package are opened, then said package is decontaminated and opened.

In the case of syringe components, it is known to use a box especially made of a polystyrene and a covering sheet made of a material marketed under the trademark TYVEKt® by DuPont de Nemours. This material is based on HDPE (high-density polyethylene) filaments, in particular bonded by means of heat and pressure.

Document U.S. Pat. No. 6,263,641 describes such a package further comprising a layer of a material which could be polyethylene, foam or plastic, this layer resting on the objects contained in the package.

For said second package, it is known to use a plastic bag, the sheet closing the window included in this bag also being made of "TYVEK®".

At its destination, after removing this second package, the box is exposed to a decontamination gas, for example, to hydrogen peroxide vapor, so as to decontaminate it. This exposure is carried out in an airlock or a tunnel for routing this box to a sterile region.

This type of decontamination is well suited for certain uses, especially for the decontamination of packages containing syringe bodies, as mentioned above. However, the applicant noticed that in some cases, there were undesirable interactions between the objects contained in the package, particularly syringe bodies, and the products with which these objects are then in contact, in particular active products or medications subsequently filling the syringe bodies.

SUMMARY OF THE INVENTION

The invention aims to overcome this considerable drawback. Its objective is therefore to provide a package for objects which are sterile or to be sterilized, which can be sterilized by means of a sterilization gas, for example of the ETO (ethylene oxide) type, and which can be decontaminated by means of a decontamination gas, for example, by means of hydrogen peroxide vapor, without there subsequently being undesirable interactions between the objects contained in the package, particularly syringe bodies, and the products with which these objects are intended to be in contact, in particular active products or medications subsequently filling the syringe bodies.

In other words, the invention aims to provide a package which is effective with regard to possible penetration of the decontamination gas, for example, of hydrogen peroxide vapor, during the decontamination process without significantly reducing the ability of this package to be sterilized by means of a sterilization gas.

The objective of the present invention is also to provide a process for producing this package.

Another object of the present invention is to provide an improved sterilization and decontamination process, using said package.

The package in question comprises, in a manner known per se, a box intended to accommodate objects which are sterile or to be sterilized and a covering sheet made of a selectively leaktight material, fastened onto the box so as to seal the latter in a leaktight manner.

According to the invention, the package comprises at least one layer of a material forming a screen which is at least partial with respect to a decontamination gas, for example, with respect to hydrogen peroxide vapor and/or able to absorb a decontamination gas, for example hydrogen peroxide vapor, this layer having a shape and dimensions such that it can be placed in the box along the covering sheet and that it lies, in this position, above the objects contained in the package, said layer or layers or the objects being mobile between a diffusion position, allowing unrestricted diffusion of the sterilization gas over, between and possibly within the objects, and a nondiffusion position, enabling restricted, or even prevented diffusion of the decontamination gas, for example, of the hydrogen peroxide vapor over, between and possibly within these same objects and in that it further comprises a plate or a grid provided with projections, shaped in order, in said diffusion position, to allow unrestricted diffusion of the sterilization gas over, between and possibly within the objects, and, in said nondiffusion position, to restrict or prevent diffusion of the decontamination gas, for example of the hydrogen peroxide vapor over, between and possibly within these same objects.

The process according to the invention for manufacturing this package comprises the steps consisting in:

using at least one material capable of forming a screen which is at least partial with respect to a decontamination gas, for example, with respect to hydrogen peroxide vapor; and/or capable of absorbing a decontamination gas, for example, hydrogen peroxide vapor, making at least one layer of this material, while choosing the shape and the dimensions of this layer such that the latter can be placed in the box along the covering sheet and that it lies, in this position, above the objects contained in the package, and making a plate or a grid provided with projections shaped in order, in a diffusion position, to allow unrestricted diffusion of the sterilization gas over, between and possibly within the objects, and, in a nondiffusion position, to restrict or prevent diffusion of the decontamination gas, for example of the hydrogen peroxide vapor over, between and possibly within these same objects.

The invention also relates to the use of the aforementioned package in a process for decontaminating this package by a decontamination gas, for example, by hydrogen peroxide vapor.

The applicant in fact noticed that hydrogen peroxide residues were found on the objects contained in the box when the sheet made of a selectively leaktight material used for its permeability to the sterilization gas was not sufficiently leaktight to the hydrogen peroxide vapor, as proved sometimes to be the case with "TYVEK®" used alone, as a covering sheet, and that these residues were the origin of the aforementioned undesirable interactions. The interactions occur all the more in the case of the syringe body, since said residues accumulate in these syringe bodies because the hydrogen peroxide vapor are heavier than the air contained in the package.

The invention provides a solution to this problem, if not totally, at least to a great extent, by providing at least one layer forming an at least partial screen against a decontamination gas, for example against hydrogen peroxide vapor, and/or capable of absorbing a decontamination gas, for example, the hydrogen peroxide vapor, which might remain in the box at the end of the decontamination process and at least a plate or a grid provided with projections shaped in order, in a diffusion position, to allow unrestricted diffusion of the sterilization gas over, between and possibly within the objects, and, in a nondiffusion position, to restrict or prevent diffusion of the decontamination gas, for example of the hydrogen peroxide vapor over, between and possibly within these same objects.

The expression "at least partial screen" means that the role of this screen is to limit, if not to prevent, the penetration of a decontamination gas, for example, of hydrogen peroxide vapor, into the package or the exchange of this gas or of this vapor between the inside and the outside of the package.

Said layer or at least one of said layers may be attached to the covering sheet, especially by adhesive bonding or welding; this or these layers are then dimensioned so as to define, on the covering sheet, a peripheral region for fastening this covering sheet to the box.

Said layer or at least one of said layers may also be simply arranged on the objects placed inside the box, prior to sealing the covering sheet, or on supports provided for this purpose, or on a part for positioning the objects, placed in this box.

The package may also comprise at least one of said layers attached to the covering sheet and at least one other of said layers arranged inside the box.

Preferably, the package comprises several layers of material in order to form said screen.

The layers may then be identical from one layer to the other. Together, they form said screen and/or make it possible to obtain the desired absorption of the decontamination gas, particularly of the hydrogen peroxide vapor.

These same layers may also be different. In this case, the package may comprise one or more layers able to form said screen and one or more layers able to carry out said absorption.

According to one possibility, the layer or layers able to form said screen are shaped in order to define, when they are in place in the box, one or more lateral or peripheral openings or interstices between their edges and the walls of the box.

These interstices or openings allow the sterilization gas to diffuse but strongly restrict the possibility of the decontamination gas, for example, of the hydrogen peroxide vapor being introduced into the package during the decontamination process. The duration and the operating conditions of this decontamination process are in fact clearly less restrictive than those of the sterilization process since, in this decontamination process, it only involves sterilizing the outer surface of the package.

To make interstices, said layer or layers may have smaller dimensions than those of the box, such that they define one or more interstices between their edges and the walls of this box; in order to make openings, this or these same layers may comprise, at their edges, notches and/or cutouts in the form of pegs.

Preferably, the package is shaped such that said layer or layers, or the objects contained in the package, are mobile between a diffusion position, allowing unrestricted diffusion of the sterilization gas over, between and possibly within the objects, and a nondiffusion position, allowing restricted, or even prevented diffusion of the decontamination gas, for example of the hydrogen peroxide vapor over, between and possibly within these same objects.

The sterilization and decontamination process according to the invention then comprises the steps consisting in:
  placing the package in the diffusion position during the sterilization process; and
  placing the package in the nondiffusion position during the decontamination process.

According to a possible embodiment of the invention in this case, the package is shaped such that said layer or layers and/or the objects go from the diffusion position to the nondiffusion position by gravity depending on whether the package is placed in a first position corresponding to the diffusion position, or whether it is placed in a second position, reversed with respect to said first position, corresponding to the nondiffusion position.

The sterilization and decontamination process according to the invention thus comprises steps consisting in:
  placing the package in a first position during the sterilization process, in which said layer or layers and the objects are in the diffusion position, such that this layer or these layers restrict only moderately, or even not at all, the diffusion of the sterilization gas over, between and possibly within the objects; and
  placing the package in a second position during the decontamination process, in which said layer or layers and the objects are in the nondiffusion position, such that this layer or these layers restrict, or even prevent, the diffusion of the decontamination gas, for example, of the hydrogen peroxide vapor over, between and possibly within these objects.

Said layer or layers can simply be mobile between a position of noncontact with the objects, corresponding to said diffusion position, and a position of contact with the objects, corresponding to said nondiffusion position.

The package comprises a plate or a grid provided with projections, shaped in order, in one position with respect to the objects, to allow said diffusion and, in another position with respect to the objects, to restrict or prevent this diffusion.

According to one embodiment of the invention, the package comprises two layers of the material marketed under the reference "TYVEK® 1073 B" by DuPont de Nemours.

According to another embodiment of the invention, the package comprises two layers of medical grade paper, especially made of a material marketed under the names "STERISHEET®", "PROPYPEL®", "ETHYPEL®", "ARPEEL®", "TALTER®" or "TRANSPEL®" by Arjo Wiggins.

According to yet another embodiment of the invention, the package comprises two layers, one of which is made of a material marketed under the reference "TYVEK® 1073 B" by DuPont de Nemours and the other is made of a medical grade paper, especially made of a material marketed under the names "STERISHEET®", "PROPYPEL®", "ETHYPEL®", "ARPEEL®", "TALTER®" or "TRANSPEL®" by Arjo Wiggins.

According to yet another embodiment of the invention, the package comprises two layers, one of which is made of a material marketed under the reference "TYVEK® 1073 B" by DuPont de Nemours and the other is made of a material marketed under the reference "TYVEK® 2FS" by DuPont de Nemours.

According to yet another embodiment of the invention, the package comprises two layers, one of which is made of a material marketed under the reference "TYVEK® 2FS" by DuPont de Nemours and the other is made of a medical grade paper, especially made of a material marketed under the name "STERISHEET®", "PROPYPEL®", "ETHYPEL®", "ARPEEL®", "TALTER®" or "TRANSPEL®" by Arjo Wiggins.

In both cases of using "TYVEK® 2FS", the smooth side of this material is preferably placed in contact with the objects contained in the package so as to restrict the access of the hydrogen peroxide vapor to the objects contained in the package, particularly to the internal volumes of these objects as in the case of a syringe body. In this case of a syringe body, the layers of "TYVEK® 2FS" rest against the proximal ends of the syringe bodies, that is to say those away from the ends accommodating the needles.

BRIEF DESCRIPTION OF THE DRAWINGS

For its proper understanding, the invention is again described below with reference to the appended schematic drawing, showing, by way of nonlimiting examples, several possible embodiments of the package to which it relates.

FIG. 1 is a view in longitudinal section according to a first embodiment, in the reversed position in which the package is placed during a process of sterilizing this package by means of a sterilization gas, especially of the ETO (ethylene oxide) type;

FIG. 2 is a view similar to FIG. 1, in an unreversed position in which the package is placed during a subsequent process of decontamination by means of hydrogen peroxide vapor;

FIG. 3 is a partial view in longitudinal section according to a second embodiment, in the reversed position in which the package is placed during said sterilization process; and FIG. 4 is a view which is similar to FIG. 3, in an unreversed position in which the package is placed during said subsequent decontamination process.

DESCRIPTION OF THE PREFERRED EMBODIMENTS

For simplification, the parts or elements of the first embodiment which are identical or similar in the second embodiment will be denoted by the same numerical references and will not be described again in detail.

FIGS. 1 and 2 show a package 1 used to transport syringe components, in particular, in the example shown, syringe bodies 2 intended subsequently to be filled by an active product or a medication.

The package 1 comprises a box 3, a covering sheet 4 sealed onto the box 3, a platen 5 not fastened to the box 3 and having barrels 12 which allow the syringe body 2 to slide freely within them, a layer 6 made of a selectively leaktight material, for example TYVEK®, and a plate 20 located between the layer 6 and the sheet 4.

The box 3 is made of polystyrene and comprises a peripheral flange 10 enabling the sheet 4 to be sealed. The flange also forms an upper shoulder 11 for accommodating the platen 5.

The covering sheet 4 is made of "TYVEK® 1073 B", a material marketed by DuPont de Nemours, based on HDPE (high-density polyethylene) filaments bonded especially by means of heat and pressure. This material is "selectively leaktight" in the sense that it is sealed to contamination of the inside of the package 1 by microorganisms, bacteria or any other biologically active material, while remaining permeable to a gas for sterilizing the inside of the package 1, for example of the ETO (ethylene oxide) type.

The plate 20 is thermoformed and has projections 21 in the form of ribs and/or pads. It also comprises a lateral skirt 22 terminated by a rim 23 lying parallel to the plane of the plate 20, the height of this skirt 22 being in particular less than the distance separating the face of the plate 5 turned towards the sheet 4 from the inner face of this sheet 4.

In practice, a platen 5 comprising syringe bodies 2 is placed in the box 3 and the layer 6 is placed on top of the syringe bodies. The plate 20 is placed on the layer 6, the projections 21 turned towards this layer 6 and the covering sheet is sealed onto the box 3. The package 1 thus constituted is placed in a second package formed by a plastic bag comprising a window closed by a sheet made of "TYVEK®", and the entire unit is placed in a cardboard box; next, this unit is sterilized by a gas of the ETO type, the package 1 being placed in the reversed position, shown in FIG. 1, during the sterilization process.

After dispatch, at its destination, the cardboard box and said second package is opened, then the package 1 is decontaminated. In order to do this, this package 1 is placed in the nonreversed position shown in FIG. 2, then it is exposed to hydrogen peroxide vapor in an airlock or a tunnel routing this package 1 to a sterile region.

As is deduced by comparing FIGS. 1 and 2, in the reversed position of the package 1 shown in FIG. 1, the platen 5 and the plate 20 move by gravity with respect to the box 3 until the plate 20 rests against the sheet 4. The syringe bodies 2 then bear against the layer 6, itself resting against the projections 21. The syringe bodies 2 bear only at points against the projections 21 such that their internal volume is not isolated from the rest of the internal volume of the package 1 and that the sterilization gas can be diffused over this entire volume, as shown by the arrow ETO. In this same position, the platen 5 is separated from the shoulder 11 and the rim 23 is at some distance from the platen 5, which also promotes the diffusion of this sterilization gas.

During the decontamination process, as shown in FIG. 2, the platen 5 comes to rest against the shoulder 11 and the rim 23 comes to rest against this platen 5, which makes it possible to restrict, or even to prevent, the diffusion of hydrogen peroxide vapor inside the volume defined by the plate 20 and the box 3. The layer 6 rests against the proximal ends of the syringe bodies 2 and contributes to limiting the possibility of these possible vapor entering the syringe bodies 2.

In the second embodiment shown in FIGS. 3 and 4, the plate 20 is in the form of a grid, that is to say it comprises a plurality of openings between the projections 21 which it comprises, and has no lateral skirt 22 or rim 23.

In this case, the package comprises a flexible nonporous layer 8 as a replacement for the layer 6, between the syringe bodies 2 and the plate 20. This layer 8 rests, during the sterilization process (cf. FIG. 3), in the spaces defined between the projections 21, such that passages exist toward the inside of the syringe body 2 in order to allow the diffusion of the sterilization gas into these bodies 2. During the decontamination process (cf. FIG. 4), the plate 20 bears against the proximal ends of the syringe bodies 2 and thus keep the layer 8 pressed against these proximal ends, which makes it possible to restrict, or even to prevent, the diffusion of the hydrogen peroxide vapor inside the syringe bodies 2.

Thus, from the above, it appears that the invention provides a decisive improvement to the prior art, by providing a package which is effective with regard to possible penetration of a decontamination gas, for example of hydrogen peroxide vapors during the decontamination process, without significantly decreasing the ability of this package to be sterilized by means of a sterilization gas; the invention also provides an improved process for sterilizing and decontaminating this package.

It goes without saying that the invention is not limited to the embodiment described above by way of example, but, on the contrary, that it encompasses all the variant embodiments falling within the scope of protection defined by the appended claims.

The invention claimed is:

1. A package intended to be used to transport objects which are sterile or to be sterilized, comprising: a box intended to accommodate the objects; a covering sheet made of a selectively leaktight material which is fastened onto the box so as to seal the box in a leaktight manner; a layer of a material forming a screen which is capable of at least one of passing a decontamination gas and being able to absorb the decontamination gas; the layer having a shape and dimensions such that the layer can be placed in the box along the covering sheet above objects contained in the package, one of said layer and the objects being mobile between a diffusion position wherein unrestricted diffusion of a sterilization gas in the package is allowed, and a nondiffusion position wherein diffusion of at least a portion of the decontamination gas is prevented from entering the package; the package further comprising a plate provided with projections, the plate being shaped in order, in said diffusion position, to allow unrestricted diffusion of the sterilization gas in the package, and, in said nondiffusion position, to prevent at least a portion of the decontamination gas from diffusing in the package.

2. The package as claimed in claim 1, wherein said layer is attached to the covering sheet, and the layer is dimensioned so as to define, on the covering sheet, a peripheral region for fastening the covering sheet to the box.

3. The package as claimed in claim 1, wherein said layer is arranged on the objects placed inside the box, prior to sealing the covering sheet.

4. The package as claimed in claim 1, wherein said layer of material comprises a pair of layers of material and wherein one of said layers is attached to the covering sheet and the other of said layers is arranged inside the box.

5. The package as claimed in claim 1, wherein said layer of material comprises a plurality of layers of material in order to form said screen.

6. The package as claimed in claim 5, wherein the layers of material forming said screen are identical from one layer to the other.

7. The package as claimed in claim 5, wherein the layers of material forming said screen are different from one layer to the other.

8. The package as claimed in claim 7, wherein the layers are shaped to define, when the layers are in place in the box, at least one of a lateral opening, a peripheral opening, and an interstice between the edges of the layers and walls of the box.

9. The package as claimed in claim 8, wherein said layers have smaller dimensions than those of the box, such that said layers define at least one interstice between edges of said layers and the walls of the box.

10. The package as claimed in claim 9, wherein said layers comprise, at their edges, one of notches and cutouts such that the notches and cutouts form openings between edges of said layers and the walls of the box.

11. The package as claimed in claim 1, wherein said one of the layer and the objects go from the diffusion position to the nondiffusion position by gravity depending on whether the package is placed in a first position corresponding to the diffusion position, or whether the package is placed in a second position, reversed with respect to said first position, corresponding to the nondiffusion position.

12. The package as claimed in claim 1, wherein the covering sheet is formed of high-density polyethylene.

13. A process of fabricating the package of claim 1 comprising the steps of: forming a screen from at least one material which is capable of at least one of passing a decontamination gas, and being able to absorb a decontamination gas; making a layer of the material having a shape and dimension such that the layer can be placed in the box along the covering sheet above the objects contained in the package; making a plate provided with projections shaped in order, in a diffusion position, to allow unrestricted diffusion of the sterilization gas in the package and, in a nondiffusion position, to prevent at least a portion of the decontamination gas from diffusing in the package.

14. The process as claimed in claim 13, further comprising the steps of: dimensioning said layer such that, when the layer is attached to the covering sheet the layer defines on this covering sheet a peripheral region for fastening the covering sheet to the box; and attaching said layer to the covering sheet.

15. The process as claimed in claim 13 further comprising the step of arranging said layer on the objects placed inside the box, prior to sealing the covering sheet.

16. The process as claimed in claim 13, wherein the layer comprises a plurality of layers, said process further comprising the steps of: dimensioning at least one of said layers such that, when the at least one layer is attached to the covering sheet the at least one layer defines on the covering sheet a peripheral region for fastening the covering sheet to the box; attaching the at least one layer to the covering sheet, and arranging at least one other layer of said plurality of layers on the objects placed inside the box, prior to sealing the covering sheet.

17. A sterilizing and decontamination process using the package as claimed in claim 1, which comprises the steps of: placing the package in the diffusion position during the sterilization process; and placing the package in the nondiffusion position during the decontamination process.

18. A sterilization and decontamination process using the package as claimed in claim 11, comprising the steps of: placing the package in a first position during the sterilization process, in which said layer and the objects are in the diffusion position, such that said layer restricts the diffusion of the sterilization gas in the package; and placing the package in a second position during the decontamination process, in which said layer and the objects are in the nondiffusion position, such that said layer restricts the diffusion of the decontamination gas in the package.

* * * * *